US00PP11521P

United States Patent [19]

Boeder

[11] Patent Number: Plant 11,521

[45] Date of Patent: Sep. 26, 2000

[54] CHRYSANTHEMUM PLANT NAMED 'MANAKIN'

[75] Inventor: Mark Boeder, West Wittering, United Kingdom

[73] Assignee: Cleangro Limited, West Sussex, United Kingdom

[21] Appl. No.: 09/133,898

[22] Filed: Aug. 13, 1998

[51] Int. Cl.[7] ..... A01H 5/00

[52] U.S. Cl. ..... Plt./298

[58] Field of Search ..... Plt./293, 298

*Primary Examiner*—Howard J. Locker

*Attorney, Agent, or Firm*—Christie, Parker & Hale, LLP

[57] ABSTRACT

A new plant variety of chrysanthemum producing small dark red flowers.

1 Drawing Sheet

BACKGROUND OF THE INVENTION

The present invention is directed to a new and distinct variety of chrysanthemum botanically classified as *Dendranthema grandiflora*. The varietal denomination of the new chrysanthemum is 'Manakin'.

The female parent of the new variety is an undistributed, unnamed seedling identified as 'G2 C27' and the male parent is a variety known as 'Tapdance'. The new variety has been asexually reproduced by vegetative cuttings in Ventura County, Calif. and the distinguishing characteristics are retained through successive generations of asexual reproduction.

SUMMARY OF THE INVENTION

'Manakin' is a compact chrysanthemum plant variety with small dark red daisy-type flowers.

COMPARISON WITH PARENTS

'Manakin' differs from the 'Tapdance' in producing small dark red flowers and a compact plant whereas 'Tapdance' produces large dark purple flowers.

BRIEF DESCRIPTION OF ILLUSTRATION

The accompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of April. 'Manakin' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. It has been observed that the shelf life of 'Manakin' is about 29 days with the response time of about 6.5 weeks. Useful growing conditions include night temperatures of about 64°–66° F., day temperatures of about 75° F. and about 5,000 foot-candles of light. The new variety blooms naturally in the middle of September in Ventura County, Calif.

Plant:

*Habit.*—Herbaceous perennial with a mounding plant form.

*Height.*—About 21 cm.

*Number of breaks from pinch.*—About 4.

*Length of lateral branches.*—About 17 cm.

*Stem color.*—Near 146D.

Foliage:

*Leaf arrangement.*—Alternate.

*Number of leaves per lateral branch.*—About 11 fully expanded leaves.

*Leaf size.*—Length: About 6 cm. Width: About 4.3 cm.

*Leaf shape.*—Ovate.

*Attachment.*—Petioled.

*Leaf apex.*—Acute.

*Base.*—Auriculate.

*Margin.*—Palmately lobed, denate.

*Aspect.*—Flat.

*Surface.*—Top: Slightly pubescent. Bottom: Pubescent. Color: Underside: Near 138B. Upperside: Near 144B.

*Petiole.*—Length: About 1.4 cm. Color: Near 144B.

*Color.*—Mature leaf: Top: Near 137A. Bottom: Near 137C. Young leaf: Top: Near 137B. Bottom: Near 138A.

Bloom:

*Inflorescence form.*—Cyme.

*Flower form.*—Daisy-type.

*Number of blooms per branch.*—About 8.

*Diameter of fully expanded bloom.*—About 3.8 cm.

*Depth of fully expanded bloom.*—About 1.6 cm, disk diameter is about 0.6 cm.

*Sepal number.*—About 32.Color: Near 138A.

*Penducle.*—Length: The lowermost penducle is typically about 7 cm long, the terminal peduncles are on average shorter, about 3 cm. Habit: Straight. Surface: Pubescent. Color: Near 138B.

*Flower Bud (when just showing color).*—Color: Near 46A. Diameter: About 1 cm. Height: About 0.9 cm. Shape: Flattened sphere.

*Ray florets.*—Number per flower: About 166. Texture: Matte. Shape: Oblong. Apex: 3 lobed, lobes obtuse. Base: Truncate. Margin: Entire. Aspect: Slightly curved. Length: About 1.5 cm. Width: About 0.6 cm.

*Disc florets.*—Number per flower: About 18. Texture: Shiny. Shape: Cylindric. Margin: Entire. Length: About 0.4 cm. Width: About 0.1 cm. Fragrance: Very faint.

Flower color:

*General flower description.*—Dark red, with small amount of yellow disc florets showing.

*Ray florets, top side.*—Immature: Near 53A. Mature: Near 46A. Fading: Near 53B.

*Ray floret, under side*.—Immature: Near 187C. Mature: Near 53A. Fading: Near 182A.

*Disc florets*.—Immature: Near 154B. Mature: Near 14B. Fading: Near 7A.

*Changes as the flower ages*.—Bloom form becomes more rounded. More disc florets are visible and flower color fades slightly.

Reproductive organs:

*Ray florets*.—Pistillate. Stigma shape: 2 forked. Stigma color: Near 7A. Style length: About 0.3 cm. Style color: Near 1D.

*Disc florets*.—Stigma shape: Linear. Stigma color: Near 12A. Style Length: About 0.4 cm. Style color: Near 4D. Stamen number: About 5. Anther length: About 0.2 cm. Pollen color: Near 12A. Pollen quantity: Moderate.

What is claimed is:

1. A new and distinct chrysanthemum plant of the variety substantially as herein shown and described.

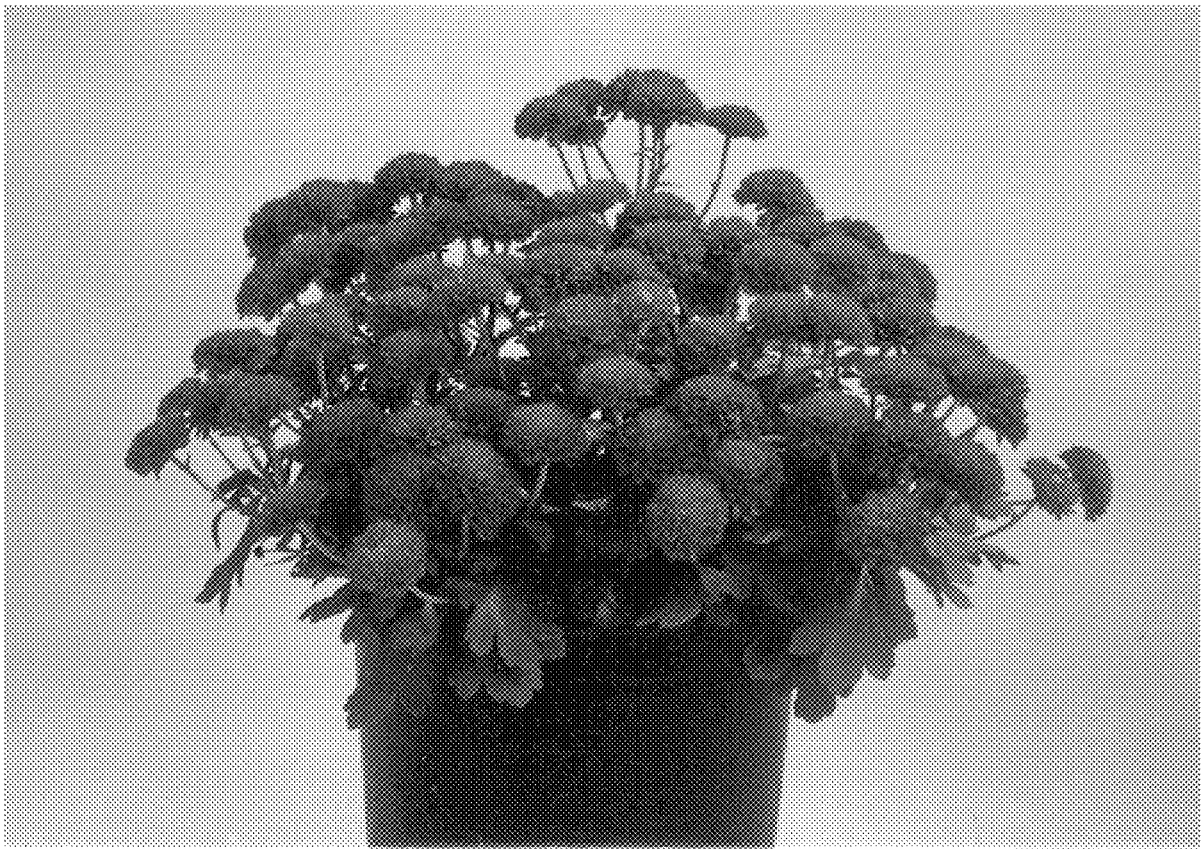

* * * * *